United States Patent [19]

Hansen et al.

[11] 4,018,660
[45] Apr. 19, 1977

[54] GAS ELECTRODE

[75] Inventors: Elo Harald Hansen, Lyngby; Jaromir Ruzicka, Naerum, both of Denmark

[73] Assignee: Zellweger Uster AG, Uster, Switzerland

[22] Filed: June 20, 1974

[21] Appl. No.: 481,047

[30] Foreign Application Priority Data

July 5, 1973  Denmark .......................... 3757/73

[52] U.S. Cl. .................... 204/195 R; 204/195 M; 204/195 G
[51] Int. Cl.² ........................................ G01N 27/46
[58] Field of Search .......... 204/1 T, 195 R, 195 M, 204/195 P, 195 G

[56] References Cited

UNITED STATES PATENTS

| | | | |
|---|---|---|---|
| 2,651,612 | 9/1953 | Haller | 204/195 R |
| 3,296,098 | 1/1967 | Arthur | 204/1 T |
| 3,380,905 | 4/1968 | Clark | 204/195 P |
| 3,429,796 | 2/1969 | Lauer | 204/195 |
| 3,479,255 | 11/1969 | Arthur | 204/1 T |
| 3,622,488 | 11/1971 | Chand et al. | 204/195 P |
| 3,649,505 | 3/1972 | Strickler et al. | 204/195 P |
| 3,686,091 | 8/1972 | Sawa et al. | 204/195 F |
| 3,713,994 | 1/1973 | Shults et al. | 204/1 T |
| 3,756,923 | 9/1973 | Dahms | 204/1 T |
| 3,761,377 | 9/1973 | Mang | 204/195 R |
| 3,886,058 | 5/1975 | Barna | 204/195 P |

*Primary Examiner*—G. L. Kaplan
*Attorney, Agent, or Firm*—Werner W. Kleeman

[57] ABSTRACT

An electrochemical cell for measuring the gas content in a solution, said electrochemical cell having a potentiometric ion sensitive electrode and a reference electrode, said electrodes being in electrochemical contact through an electrolyte solution, said electrolyte solution forming a thin, continuous, stabilized, stationary layer covering the surface of said ion sensitive electrode so that said thin electrolyte layer is in direct physical contact with a gaseous phase.

13 Claims, 3 Drawing Figures

GAS ELECTRODE

The present invention relates to an electrochemical cell which can be used for the measurement of gases.

The possibility to measure quantitatively gases such as ammonia ($NH_3$), carbon dioxide ($CO_2$), sulphur dioxide ($SO_2$) and hydrogen sulphide ($H_2S$) is of major importance within e.g., the fields of industrial and clinical chemical analysis. During the last few years the need for reliable sensors for gas measurements has especially been accentuated by the trends within the area of pollution analysis. In addition, it is often essential to be able to determine the content of salts such as ammonium compounds, carbonates, sulphites and sulphides in aqueous solutions.

A series of electrochemical sensors have been suggested and developed for this purpose, all of them generally based upon the principle of the well-known potentiometric carbon dioxide sensor, utilizing a glass electrode and a reference electrode joined by an aqueous electrolyte solution containing hydrogen carbonate ions. The two electrodes and the electrolyte are separated from the sample medium by means of a hydrophobic membrane which is permeable to carbon dioxide, but relatively impermeable to the aqueous solution. The glass electrode in conjunction with the reference system thus measures the hydrogen ion activity in the electrolyte, this activity being proportional to the logarithm of the partial pressure of carbon dioxide in the sample, which pressure in turn can be related to the concentration of carbon dioxide or carbonate in the sample into which the sensor is immersed during the measurement. Typical use of the carbon dioxide is in the determination of the carbon dioxide content of blood ("Acid Base Physiology in Medicine", by R. W. Winters et al., Radiometer A/S, Copenhagen, 1967). The theoretical background for the mode of operation of such a sensor, including the choice of a suitable hydrogen carbonate ion concentration in the electrolyte solution, is well known (see e.g., D. J. G. Iven and G. J. Janz "Reference Electrodes, Theory and Practice", Academic Press, New York, 1961, p. 498), and has been generalized for the determination of other gases, which in a similar way give rise to a change of the hydrogen ion activity in a suitable electrolyte solution. Thus, sensors for the determination of sulphur dioxide and ammonia are now commercially available, and a recent patent, U.S. Pat. No. 3,649,505 of Mar. 14, 1972 (dealing with an ammonia sensor) may therefore serve as an illustration of the present state of development.

It is characteristic, however, that all patents within this field have focused upon the material of the hydrophobic membrane which separates the electrolyte solution from the sample solution, which for instance may be blood, serum, or an aqueous solution into which the sensor is immersed. Various membrane materials have been suggested, such as polytetrafluoroethylene (the U.S. Pat. No. 3,649,505 mentioned above), fluorinated ethylenepropylene and — most recently — polyvinylidene fluoride microporous filter material. In the nature of things, these membrane materials must be hydrophobic, and their thickness (ca. 0,015 cm), pore size (not larger than 1.5 $\mu$), density, porosity homogeneity, and chemical composition are consistently the central parts in the patent claims, since the function of the membranes is to prevent a direct physical contact between the electrolyte solution and the sample solution, but at the same time allow free passage of gas from the latter to the former solution. However, if the pores in the membrane become clogged either by electrolyte and/or sample solution (which invariably will happen if a surfactant is present, or if the membrane is subjected to excessive pressures during mounting), the sensor will immediately cease to function. Furthermore, the membrane material has a decisive effect upon the speed with which the sensor responds to changes in the sample solution ("speed of response"), which parameter additionally deteriorates during the application of the sensor, especially if the sample solution contains finely dispersed material that may be adsorbed on the surface of the hydrophobic membrane.

SUMMARY OF THE INVENTION

The central part of the invention described here is a simplification in the construction of a potentiometric gas sensor with the aim of obtaining the fastest possible electrode response and to avoid the interferences and limitations which might be caused by the characteristics, the quality and the condition of the generally used membranes.

We therefore suggest that the application of any form of hydrophobic membrane is avoided, so that the electrolyte layer which covers the surface of the ion-sensitive electrode is brought into direct physical contact with the gas which is to be measured. In order to prevent a direct physical contact between said electrolyte solution and the aqueous sample solution, in which the gas to be measured is generated, the (gaseous phase-) distance between said electrolyte solution and the sample solution is adjusted so that these two solutions do not touch each other during the measuring operations. Because the diffusion of gases in air (gaseous phase) is very much faster than in solid, aqueous or even porous media, it is not essential to adjust said distance between the electrolyte solution and the sample solution to any particularly low value, since the diffusion of gas in the gaseous phase over a distance of several centimeters occurs very much faster than over a distance of a fraction of a millimeter in a porous membrane whose content of solid material impedes the diffusion process (thus e.g., ammonia, the gaseous diffusion coefficient of which is 16.9 at 20° C, will at this temperature diffuse over a distance of 3 cm within 0.34 min.).

Besides reaching the maximum speed of response, the following advantages have been gained with the electrochemical cell described in the present patent:

a. The construction of the sensor is very simple (FIG. 1).

b. The dependability and the reliability of the measurement is substantially increased as the sensor does not come into direct physical contact with the sample solution; thus there is no interference due to the presence in the sample solution of e.g., surfactants of particulate matter.

c. The life time of the sensor is substantially increased; and the electrolyte layer or thin-film can be easily and rapidly renewed or changed.

d. A versatile electrode system has been obtained, which can be used for measuring different gases by successively changing the electrolyte layer, or the ion-sensitive electrode, or both — without having to consider any peculiarities between a hydrophobic membrane and the particular gas.

An important aspect of the present invention is the stabilization of the thin layer or thin-film of electrolyte which covers the surface of the ion-sensitive electrode and at the same time provides the electrochemical contact with the reference electrode. There are two essential requirements which must be satisfied:

a. Time constant composition of the electrolyte layer on the electrode surface.
 b. Minimum thickness of the electrolyte layer.

The former of these factors effects the reproducibility and the sensitivity of the measurements, while the latter effects the speed with which the electrode reacts ("speed of response"). The following ways of optimizing these two parameters were found to be applicable:

a. By keeping the partial pressure of water (relative humidity) above the sample solutions at a relatively constant level in the individual sample containers, and by storing the sensor between measurements either in a similar sample container above the same relative humidity or directly in a solution of the respective electrolyte.
 b. By adding to the electrolyte solution a non-ionic wetting agent or surfactive compound.
 c. By covering the surface of the ion-sensitive electrode with a hydrophilic material such as cellophane or silicagel, which, soaked with electrolyte solution, serves as a mechanical support for this solution.

A combination of (a) and (b) is greatly to be preferred since this combination allows the formation of an extremely thin layer (film) of electrolyte on the electrode surface, resulting in a very fast electrode response as said thin electrolyte film will equilibrate almost instantly with a gas present, while a thicker electrolyte layer — as given by (c) — will yield a slower electrode response.

The frequency with which the electrolyte layer or thin-film has to be renewed depends upon the measurement technique used and the electrolyte used. By discrete sample measurements the electrode surface may be renewed simply by permitting the electrode to be in contact with the respective electrolyte solution between the individual measurements. This has the added advantage that a constant base line signal is obtained after each measurement, which signal then can serve as reference point. This course of procedure is, however, not a necessity, as demonstrated in Example I and in FIGS. 2 and 3. By continuous monitoring or continuous flow-measurements it is only necessary to obtain and secure a constant relative degree of humidity in the measured stream (which normally will be satisfied) and/or renew said thin film or layer of electrolyte either periodically or continuously.

BRIEF DESCRIPTION OF THE DRAWINGS

The invention will be better understood and objects other than those set forth above, will become apparent when consideration is given to the following detailed description thereof. Such description makes reference to the annexed drawings wherein.

Figure 1:
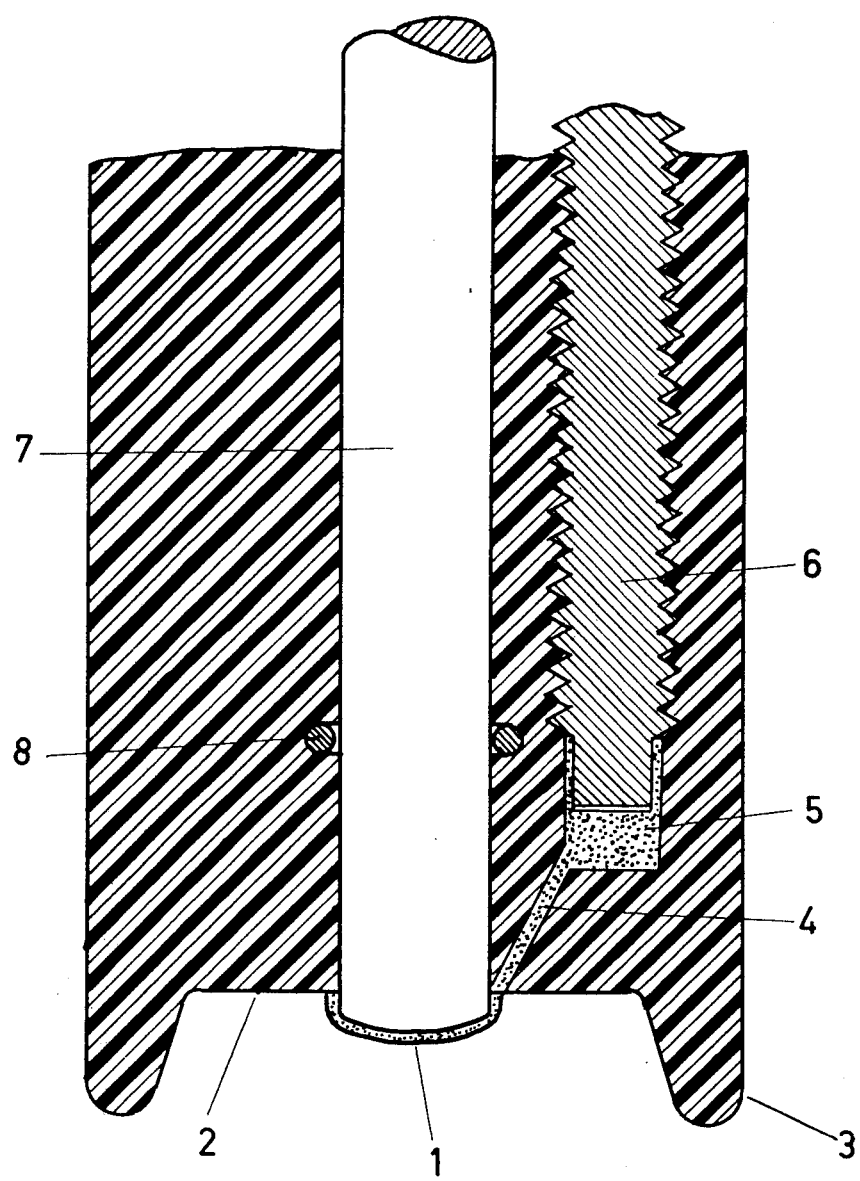
FIG. 1 is a partial longitudinal sectional view through a gas sensor constructed according to the invention.

DETAILED DESCRIPTION OF THE INVENTION for comprehensive understanding of the present invention, reference is made to FIG. 1 which shows a partial longitudinal sectional view of the gas sensor constructed in accordance with the invention described herein, comprising the electrode body (made of polyethylene, polytetrafluoroethylene or polymethylmethacrylate) which accomodates the ion-sensitive electrode 7 secured in position by an O-ring 8, a reference electrode 6 mounted in the electrode body, the reference electrode containing a humidified inorganic salt such as potassium chloride or potassium nitrate containes within a chamber or cavity 5, which is in contact with a ceramic porous pin, or plug 4, which in turn is in contact with a thin film or layer 1 of an electrolyte solution covering the surface of the ion-sensitive electrode 7. The flat part 2 of the electrode body serves as a lid for a measuring chamber or measuring vessel or container (not shown here) and can possibly be supplied with a rubber or plastic washer (ring) in order to prevent any leakage of gas from the measuring chamber. The jutting or protruding edge 3 serves to protect the electrode surface with the electrolyte film or layer 1 against any mechanical damage.

It is to be understood, of course, that the arrangement shown by way of example in FIG. 1 only serves as a suggestion for an applicable sensor construction, but inherently there is nothing to prevent the utilization of other proportions of the individual parts of the construction. For instance, the height and the diameter of the electrode body are of less importance, and so is the dimension of the edge 3.

EXAMPLE I

Figure 2:
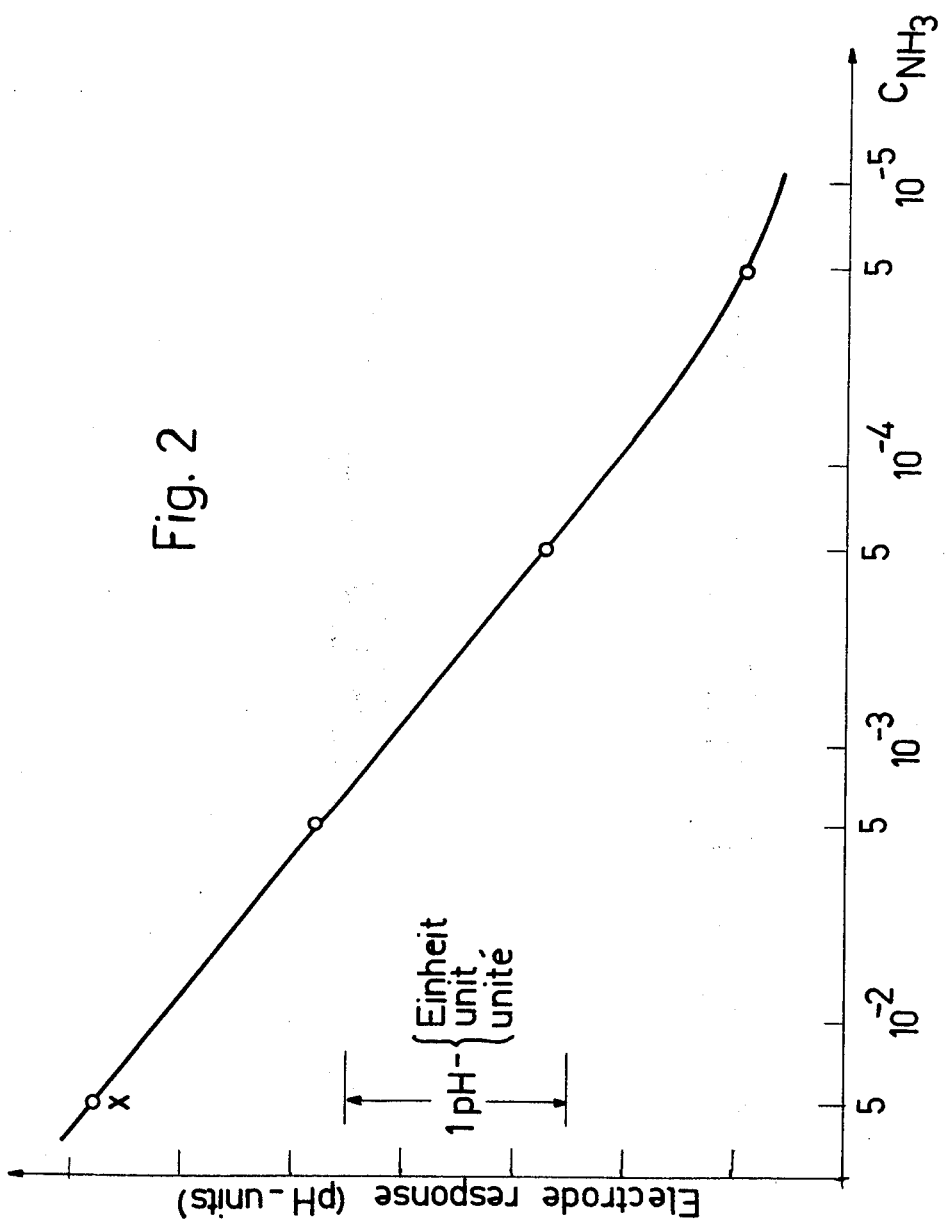
FIG. 2 is a graph representing the results obtained when using the gas sensor of FIG. 1 during a $NH_3$-measurement.
Figure 3:
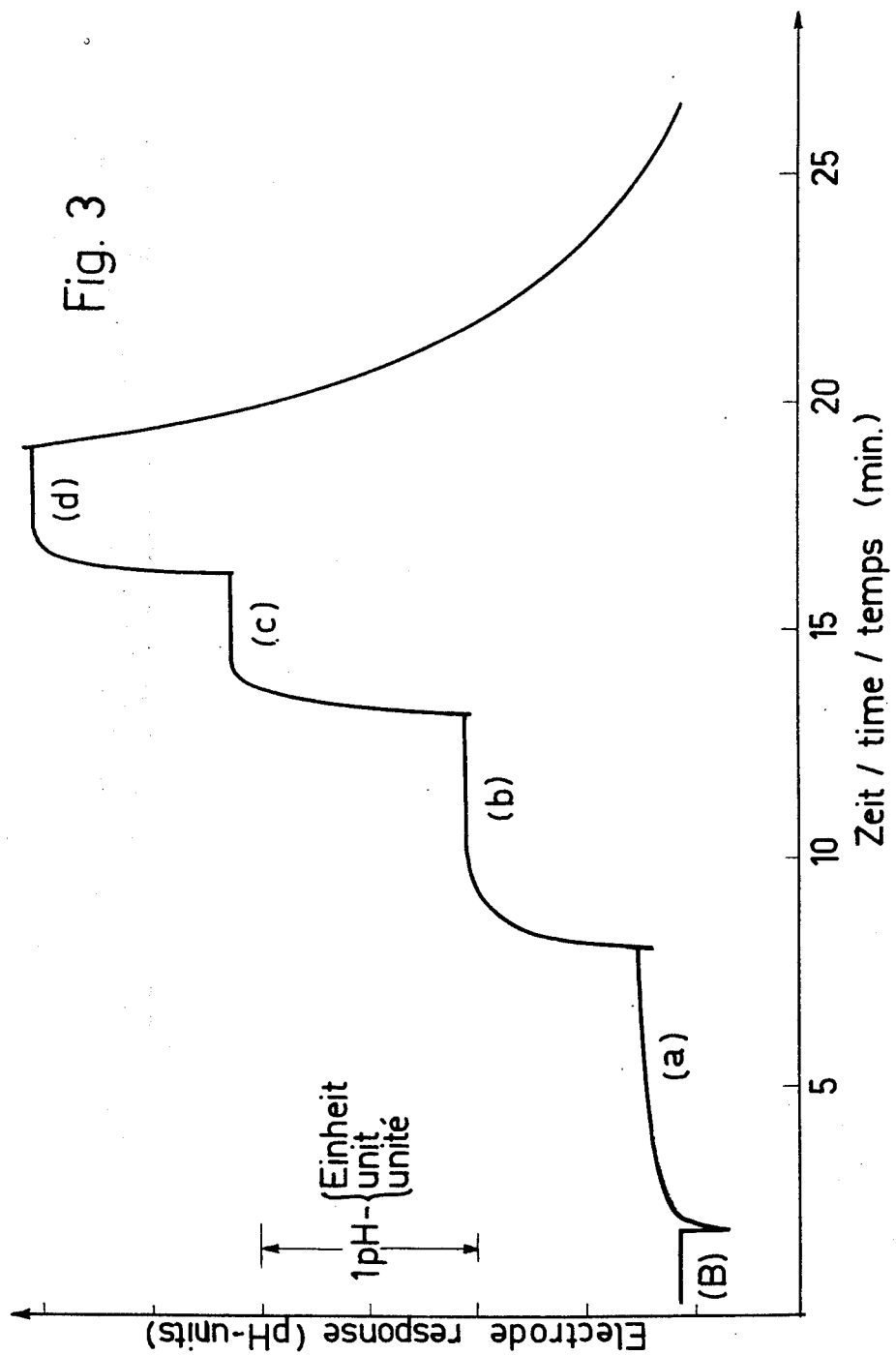
FIG. 3 is a graphic illustration of the measurement data forming the basis of the values obtained in the graph of FIG. 2.

FIG. 2 is a graphical representation showing data obtained with an ammonia sensor constructed as depicted in FIG. 1, where the ion-sensitive electrode 7 is a pH-sensitive glass electrode and where the electrolyte solution in the thin film or layer 1 consisted of a solution of 0.20 F $NH_4Cl$ and 0.20 F KCl saturated with Victawet 12 (Stauffer Chemical Company, Specialty Chemical Division, New York, NY 10017, USA) serving as wetting agent. The individual points in the plot in FIG. 2 are determined on the basis of FIG. 3 which shows the actual output trace on a recorder which is connected to the ammonia sensor through a potentiometer, the ammonia sensor being successively used to measure the following solutions: (B): blank (6 ml 0.2 F borax); (a): 3ml $10^{-4}$ F $NH_4Cl$ + 3 ml 0.2 F borax; (b): 3 ml $10^{-3}$ F $NH_4Cl$ + 3 ml 0.2 F borax; (c): 3 ml $10^{-2}$ F $NH_4Cl$ + 3 ml 0.2 borax; and (d): 3 ml $10^{-1}$ F $NH_4Cl$ + 3 ml 0.2 F borax; and where the distance between the surface of the ion-sensitive electrode ((1), FIG. 1) and the sample solution was approximately 1 cm during the measuring operations. The pH-value in the sample solutions (B) to (c) was 9.20 while the pH-value in sample solution (d) was 9.10. This value is corrected in FIG. 2 to pH = 9.20. Both in FIG. 2 and in FIG. 3 absolute values have been omitted on the ordinate axis, the differential changes being expressed in pH-units. The measurements were executed as discrete determinations; that is, having measured solution (d) the electrode was again placed above solution (B). The temperature was 25° C.

In the ideal situation the cell should yield a Nernstian response of 1 pH-unit for each decade of concentration change, which it — as is apparent from FIG. 2 — was found to do exactly in the range down to ca. $5.10^{-5}$ F $NH_3$. (It should be added, however, that by using a weaker ammonium chloride formality in the electrolyte solution it would have been possible to decrease this lower limit further).

EXAMPLE II

By applying the same sensor as in Example I, that is, provided with a pH-sensitive glass electrode, but now provided with an electrolyte solution consisting of $1.10^{-2}$ F $NaHCO_3$ + $1.10^{-1}$ F KCl saturated with Victawet 12 non-ionic wetting agent, the total content of carbonate in a series of solutions containing from $1.10^{-4}$ to $1.10^{-2}$ mol/1 of carbonate was determined; immediately prior to measurement, sodium hydrogenophosphate solution of pH 6.5 was added to each of the aqueous carbonate solutions in order to liberate the carbon dioxide. By using a microchamber with a total volume of 3 $cm^3$, with a distance of 3 mm between the sample solution and the electrode surface ((1), FIG. 1), it was possible to reproducibly determine the carbonate content in sample volumes as small as 50 /$\mu$l.

EXAMPLE III

By using the same technique as mentioned in Example I, but now using a silver ion-sensitive electrode provided with a solution of 0.10 $H_2SO_4$ saturated with Victawet 12 non-ionic wetting agent, this solution serving as electrolyte, it was possible to reproducibly measure the sulphide content — as generated as $H_2S$ in aqueous solutions of $Na_2S$ to which 0.1 F $H_2SO_4$ was added — in the concentration range of $5.10^{-5}$ to $1.10^{-1}$ F $Na_2S$.

Further examples regarding the application of a silver ion-sensitive electrode for measuring e.g., hydrogen cyanide or dicyan, or of a platinum electrode for determining oxidizing or reducing gasses by means of other electrolyte solutions are not described here as they are obvious through well-known theoretically described ion equilibriae and redox conditions in electrolytic solutions.

Although several embodiments of the invention have been disclosed herein for purposes of illustration, it will be understood that further variations and modifications of the structures, materials and uses disclosed and discussed herein may be made without departing from the spirit of the invention, the scope of which is defined by the following claims:

What is claimed is:
1. An electrochemical cell for measuring the gas content in a sample solution by pH measurement without immersing said electrochemical cell in said sample solution, said electrochemical cell comprising an ion-sensitive electrode and a reference electrode, an electrolyte solution for placing said ion-sensitive electrode and reference electrode in electrochemical contact with one another, said electrolyte forming a continuous, stabilized, stationary thin-film covering at least a portion of the surface of said ion-sensitive electrode, said electrolyte solution being retained in a chamber, said chamber communicating with said stationary thin-film through the agency of a porous plug, said thin-film of electrolyte solution covering said surface portion of the ion-sensitive electrode having an exposed surface which is adapted to be in direct physical contact with the gas evolved from said sample solution.

2. The electrochemical cell as defined in claim 1, wherein the thickness of said thin-film does not exceed two millimeters.

3. The electrochemical cell as defined in claim 1, wherein at least one component of the electrolyte solution is an ionizable chemical compound.

4. The electrochemical cell as defined in claim 1, wherein said thin-film covering the ion-sensitive electrode is stabilized by means of a non-ionic surfactive compound.

5. The electrochemical cell as defined in claim 1, wherein said thin-film covering said ion-sensitive electrode is stabilized by a hydrophilic solid material.

6. The electrochemical cell as defined in claim 5, wherein said hydrophilic solid material is a layer of cellophane.

7. The electrochemical cell as defined in claim 5, wherein the hydrophilic solid material is a layer of gelatine.

8. The electrochemical cell as defined in claim 1, wherein said thin-film is stabilized by means of a non-ionic surfactive compound and a hydrophilic solid material.

9. The electrochemical cell as defined in claim 1, wherein the ion-sensitive electrode comprises a hydrogen ion-sensitive electrode to permit use of the electrochemical cell for measuring ammonia ($NH_3$), carbon dioxide ($CO_2$), sulphur dioxide ($SO_2$), or hydrogen sulphide ($H_2S$), wherein each of such gases causes a change in the hydrogen ion activity in the thin-film of electrolyte solution which covers said surface portion of the ion-sensitive electrode.

10. The electrochemical cell as defined in claim 1, wherein the ion-sensitive electrode comprises a silver ion-sensitive electrode for sensing the gas quantity in a sample due to a change in the silver ion activity in the thin-film of electrolyte solution covering said surface portion of said ion-sensitive electrode.

11. The electrochemical cell as defined in claim 1, wherein the ion-sensitive electrode comprises a platinum electrode serving as a redox sensor for sensing reducing or oxidizing gases through the change in the redox level in the thin-film of the electrolyte solution covering the ion-sensitive electrode.

12. The electrochemical cell as defined in claim 1, wherein the ion-sensitive electrode is a hydrogen ion-sensitive electrode.

13. An electrochemical cell for measuring the gas content of a sample solution in a container by pH measurement without immersing said electrochemical cell in said sample solution, comprising an ion-sensitive electrode and a reference electrode, an electrolyte solution for placing said ion-sensitive electrode and reference electrode in electrochemical contact with each other, said electrolyte solution forming a stationary thin-film of electrolyte covering at least a portion of the surface of said ion-sensitive electrode, said electrolyte solution being retained in a chamber, said chamber communicating with said stationary thin-film through the agency of a porous plug, said thin-film of electrolyte solution covering said surface portion of the ion-sensitive electrode having an exposed surface disposed so as to be in direct physical contact with the gas evolved at the surface of the sample solution in the container, said cell including means for supporting said cell at said container with the exposed surface of said thin-film of electrolyte solution in spaced, superposed relation to the surface of the sample solution.

* * * * *